United States Patent
Wujciak et al.

(10) Patent No.: US 10,667,678 B2
(45) Date of Patent: Jun. 2, 2020

(54) EAR INSTRUMENT ASSEMBLY

(71) Applicant: Anna J. Wujciak, Fenton, MI (US)

(72) Inventors: Anna J. Wujciak, Fenton, MI (US); Jennie C. Wang, Chicago, IL (US); Brandon J. Hudik, Bordentown, NJ (US); Caroline N. Jones, New York, NY (US)

(73) Assignee: Anna J. Wujciak, Fenton, MI (US)

( * ) Notice: Subject to any disclaimer, the term of this patent is extended or adjusted under 35 U.S.C. 154(b) by 98 days.

(21) Appl. No.: 15/949,683

(22) Filed: Apr. 10, 2018

(65) Prior Publication Data

US 2019/0307322 A1    Oct. 10, 2019

(51) Int. Cl.
| | |
|---|---|
| *A61B 1/00* | (2006.01) |
| *A61B 1/227* | (2006.01) |
| *A61B 1/045* | (2006.01) |
| *A61B 1/06* | (2006.01) |
| *A61B 1/05* | (2006.01) |

(52) U.S. Cl.
CPC .......... *A61B 1/227* (2013.01); *A61B 1/00011* (2013.01); *A61B 1/00128* (2013.01); *A61B 1/045* (2013.01); *A61B 1/051* (2013.01); *A61B 1/0661* (2013.01); *A61B 1/00034* (2013.01)

(58) Field of Classification Search
CPC ..... A61B 1/227; A61B 1/00011; A61B 1/121; A61B 1/00128; A61B 1/00131; A61B 1/045
See application file for complete search history.

(56) References Cited

U.S. PATENT DOCUMENTS

| | | | |
|---|---|---|---|
| 1,775,140 A | 9/1930 | Platou |
| 2,331,732 A | 10/1943 | Ryzmek |
| 3,110,304 A | 11/1963 | Hartman |
| 3,651,808 A | 3/1972 | White |
| 3,698,387 A | 10/1972 | Moore et al. |
| 4,566,439 A | 1/1986 | Burgin |

(Continued)

FOREIGN PATENT DOCUMENTS

| | | |
|---|---|---|
| EP | 1337228 B1 | 7/2005 |
| WO | 2002056756 A2 | 7/2002 |

OTHER PUBLICATIONS

Firefly DE550 Wireless Digital Video Otoscope/Earscope, with 50x magnification and built-in battery; Firefly Global; https://www.amazon.com/dp/B005BD3N5A/ref=asc_df_B005BD3N5A5247010/?tag=hyprod-20&creative=395033&creativeASIN=B005BD3N5A&linkCode=df0&hvadid=193163886136&hvpos=1o2&hvnetw=g&hvrand=5268749797869875143&hvpone=&hvptwo=&hvqmt=&hvdev=c&hvdvcmdl=&hvlocint=&hvlocphy=9003367&hvtargid=pla-307188028260; accessed Mar. 20, 2018; 6 pages.

(Continued)

*Primary Examiner* — Julianna N Harvey
*Assistant Examiner* — Christina Negrellirodriguez
(74) *Attorney, Agent, or Firm* — Quinn IP Law (57) ABSTRACT

An ear instrument assembly includes a base unit and a tool. The base unit includes a first housing defining an opening. The tool is movable between a storage position in which the tool is partially disposed into the opening such that the tool is secured to the first housing and a use position in which the tool is removed from the opening such that the tool is spaced from the first housing. The tool includes a tip contained inside the first housing when the tool is in the storage position. The tool includes a camera at least partially disposed in the tip of the tool, and the tool includes a curette attachable to and detachable from the tip of the tool.

16 Claims, 6 Drawing Sheets

(56) References Cited

U.S. PATENT DOCUMENTS

| | | | |
|---|---|---|---|
| 4,785,796 | A | 11/1988 | Mattson |
| 5,363,839 | A | 11/1994 | Lankford |
| 5,374,276 | A | 12/1994 | Lay |
| 5,662,605 | A | 9/1997 | Hurwitz |
| 6,106,457 | A | 8/2000 | Perkins et al. |
| 6,155,987 | A | 12/2000 | Scherl |
| 6,319,199 | B1 | 11/2001 | Sheehan et al. |
| 8,062,216 | B2 | 11/2011 | Raghuprasad |
| 8,777,972 | B2 | 7/2014 | Burres |
| 2011/0066172 | A1 | 3/2011 | Silverstein |
| 2015/0351606 | A1 | 12/2015 | Ruppersberg et al. |
| 2015/0351607 | A1 | 12/2015 | Ruppersberg et al. |
| 2015/0351616 | A1 | 12/2015 | Ruppersberg et al. |
| 2015/0351620 | A1 | 12/2015 | Ruppersberg et al. |
| 2015/0351637 | A1 | 12/2015 | Ruppersberg et al. |
| 2015/0374208 | A1 | 12/2015 | Ruppersberg et al. |
| 2017/0209078 | A1 | 7/2017 | Hoberman et al. |
| 2018/0125345 | A1* | 5/2018 | Rebella .............. A61B 1/00082 |
| 2018/0256013 | A1 | 9/2018 | Ruppersberg et al. |

OTHER PUBLICATIONS

Digital Ear Endoscope, ScopeAround USB, https://www.amazon.com/dp/B075GJPJYR/ref=sspa_dk_detail_1?psc=1; accessed Mar. 20, 2018; 8 pages.

Welch Allyn 11840-A6 iExaminer Adapter for iPhone 6 & 6s for Panoptic Ophthalmoscope; https://www.google.com/shopping/product/14111693018872423573?q=digital+otoscope+phone&rlz=1C1GGRV_enUS751US756&biw=2400&bih=1367&sa=X&ved=0ahUKEwjntZywu6LXAhVB5CYKHXcEAooQ8wlIvwlwAA; accessed Mar. 20, 2018; 2 pages.

How Debrox Works; http://www.debrox.com/en/Debrox_and_How_it_Works.html; Prestige Brands, Inc.; copyright 2018; accessed Mar. 20, 2018; 5 pages.

ADC products; http://adctoday.com/learningcenter/about-otoscopes/anatomy-otoscope; American Diagnostic Corporation; copyright 2018; accessed Mar. 20, 2018; 5 pages.

Otoscopes; http://www.audiologyonline.com/articles/otoscopes-833; Audiology Online; dated May 9, 2011; 16 pages.

https://www.oaktreeproducts.com/perfect-full-size-otoscope; Oaktree Products; copyright 2018; accessed Mar. 20, 2018; 4 pages.

Wireless Video Otoscope; http://fireflyglobal.com/; Firefly Global; copyright 2015; accessed Mar. 20, 2018; 3 pages.

Ear Wax Removal; http://www.medline.com/category/Ear-Wax-Removal/cat500091; Medline Industries, Inc.; copyright 2017; accessed Mar. 20, 2018; 3 pages.

Otoscope Batteries; https://www.oaktreeproducts.com/otoscope-batteries; Oaktree Products; copyright 2018; accessed Mar. 20, 2018; 11 pages.

Memory: Myth or Fact?; http://batteryuniversity.com/learn/archive/memory_myth_or_fact; accessed Mar. 20, 2018; 8 pages.

Getty Images; https://www.gettyimages.com/detail/photo/baby-getting-ear-checked-with-otoscope-royalty-free-image/183418226; accessed Mar. 20, 2018; 7 pages.

The effectiveness of topical preparations for the treatment of ear-wax: a systematic review; British Journal of General Practice; http://bjgp.org/content/54/508/862; copyright 2004; accessed Mar. 20, 2018; 17 pages.

Over the counter healthcare & cleaning products from Prestige Brands; http://www.prestigebrands.com/products/eye-ear-nose-throat/murine-ear-wax-removal/en/How_It_Works.html; Prestige Brands, Inc.; copyright 2018; accessed Mar. 20, 2018; 17 pages.

OtoClear Ear Irrigation Tips & Systems; Bionix; https://www.bionix.com/medicaltech/product/otoclear-ear-irrigation/; accessed Mar. 20, 2018; 5 pages.

Gleanings from a professional lifetime of cleaning out kids' ear canals; Healio Infectious Diseases in Children; https://www.healio.com/pediatrics/respiratory-infections/news/online/%7B322fa4bc-e678-4913-96a1-c3c7491b06b1%7D/gleanings-from-a-professional-lifetime-of-cleaning-out-kids-ear-canals; dated Feb. 1, 2011; 6 pages.

Welcome to the Steam Discussions; http://steamcommunity.com/discussions/; accessed Mar. 20, 2018; 3 pages.

Our Little Nest; Ear Infections and Antibiotics; http://theashleyslittlenest.blogspot.com/2013/10/ear-infections-and-antibiotics.html; dated Oct. 30, 2013; 5 pages.

How to Clear Your Ears, Best Way, With Q Tips, Hydrogen Peroxide, Baby Oil or Candle and Impacted Ear Wax Removal; http://www.lightskincure.org/ear/hot-to-clean-your-ears-best-way-q-tips-hydrogen-peroxide-candle/; accessed Mar. 20, 2018; 14 pages.

\* cited by examiner

EAR INSTRUMENT ASSEMBLY

INTRODUCTION

During diagnosis of ear maladies and cerumen removal, it is desirable that a physician is able to visualize various regions of the ear such as the tympanic membrane. The size and shape of the ear canal, the patient's sensitivity, as well as the presence of cerumen, can make visualization difficult. An otoscope is used to gain a better view of the ear canal, cerumen, and tympanic membrane. However, otoscopes are often held similar to a hammer which can be bulky and challenging to maneuver. Otoscopes can block quite a bit of space at the opening of the ear canal, which can make viewing into a child's ear more challenging because a child's ear is smaller, children tend to move more, and an otoscope can be a frightening object to a child. Therefore, additional time is usually required trying to calm and/or secure the position of the child patient to view the ear canal or tympanic membrane.

Generally, otoscopes are utilized to view inside of the patient's ear, but a separate process is utilized to remove cerumen in the ear canal which precludes continuous visualization into the ear canal. Therefore, viewing into the ear canal is utilized to determine a course of action but the otoscope is removed from the patient's ear for the next process. Therefore, for example, if cerumen is to be removed, the ear canal can be irrigated with water or a solution, or a curette can be utilized to scrape/scoop out the cerumen. After this process, the otoscope can be utilized again to see if all of the cerumen has been removed or whether more irrigation/scraping is needed. This process is repeated until the desired outcome is achieved. Repeating the process to remove cerumen can cause irritation of the tissue inside the channel.

SUMMARY

The present disclosure provides an ear instrument assembly including a base unit and a tool. The base unit includes a first housing defining an opening. The tool is movable between a storage position in which the tool is partially disposed into the opening such that the tool is secured to the first housing and a use position in which the tool is removed from the opening such that the tool is spaced from the first housing. The tool includes a tip contained inside the first housing when the tool is in the storage position. The tool includes a camera at least partially disposed in the tip of the tool, and the tool includes a curette attachable to and detachable from the tip of the tool.

The present disclosure also provides an ear instrument assembly in communication with an external device. The ear instrument assembly including a base unit configured to be in communication with the external device. The base unit includes a first housing defining an opening. The ear instrument assembly also includes a tool movable between a storage position in which the tool is partially disposed into the opening such that the tool is secured to the first housing and a use position in which the tool is removed from the opening such that the tool is spaced from the first housing. The tool further includes a tip contained inside the first housing when the tool is in the storage position. The tool also includes a camera at least partially disposed in the tip of the tool. The tool includes a curette attachable to and detachable from the tip of the tool. The tip of the tool defines an aperture coaxial with a central axis. The camera is aligned coaxial with the central axis. The tip further includes an inner surface defining an outer boundary of the aperture, with the inner surface facing the central axis. The tip includes an outer surface opposing the inner surface and facing away from the inner surface. The tool further includes a light disposed between the camera and the inner surface of the tip. The camera and the light are disposed in the aperture. The curette includes an arm extending along a longitudinal axis and includes a fastener member secured to the arm. The fastener member is attachable to and detachable from the outer surface of the tip of the tool. The fastener member includes a c-shaped clip. The curette includes an extractor member secured to the arm. The c-shaped clip and the extractor member are spaced from each other. The extractor member extends from the arm at an angle not equal to zero degrees relative to the longitudinal axis and not equal to one-hundred eighty degrees relative to the central axis. The tool includes a power source and coils that are electrically connected to the power source. The coils define a hole coaxial with the central axis. The tool includes a wire harness disposed through the hole to electrically connect the camera and the light to the power source. The tool includes a charge-couple-device (CCD) camera module in communication with the camera, and the wire harness electrically connects the camera and the CCD camera module. The tool includes a transmitter in communication with the CCD camera module, with the CCD camera module and the transmitter electrically connected to the power source. The tool includes an antenna in communication with the transmitter to transmit data gathered from the camera. The base unit includes an antenna configured to receive the data from the antenna of the tool regarding the data gathered by the camera. The base unit includes a receiver in communication with the antenna of the base unit. The base unit includes a voltage divider in communication with the receiver. The base unit includes a screen decoding board in communication with the voltage divider. The base unit includes a controller having a processor in communication with the screen decoding board. The controller is configured to stream the data from the camera to the external device that displays the data from the camera. The first housing of the base unit includes a face configured as a monkey face, and the second housing of the tool is configured as a banana.

The detailed description and the drawings or FIGS. are supportive and descriptive of the disclosure, but the claim scope of the disclosure is defined solely by the claims. While some of the best modes and other embodiments for carrying out the claims have been described in detail, various alternative designs and embodiments exist for practicing the disclosure defined in the appended claims.

DETAILED DESCRIPTION

Those having ordinary skill in the art will recognize that all directional references (e.g., above, below, upward, up, downward, down, top, bottom, left, right, vertical, horizontal, etc.) are used descriptively for the FIGS. to aid the reader's understanding, and do not represent limitations (for example, to the position, orientation, or use, etc.) on the scope of the disclosure, as defined by the appended claims. Furthermore, the term "substantially" can refer to a slight imprecision or slight variance of a condition, quantity, value, or dimension, etc., some of which that are within manufacturing variance or tolerance ranges. The phrase "at least one of" as used herein should be construed to include the non-exclusive logical "or", i.e., A and/or B and so on depending on the number of components.

Figure 1:
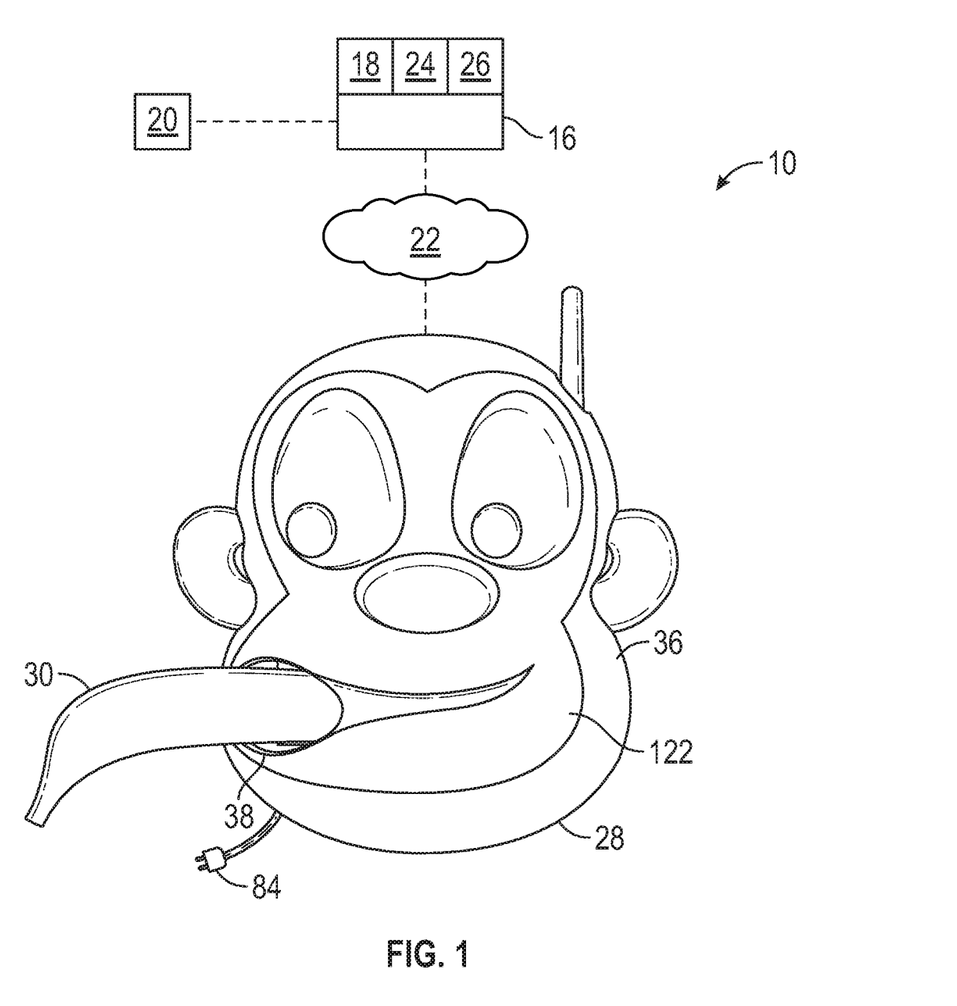
FIG. 1 is a schematic illustration of an ear instrument assembly including a base unit and a tool in a storage position.

Referring to the FIGS., wherein like numerals indicate like or corresponding parts throughout the several views, an ear instrument assembly 10 is generally shown in FIG. 1. Generally, the ear instrument assembly 10 provides visualization into a channel 12 (see FIG. 2), such as an ear canal of a person, as well as a way to remove cerumen 14 (see FIG. 2) from the ear canal by utilizing the real time visualization as discussed further below.

Continuing with FIG. 1, the ear instrument assembly 10 is in communication with the external device 16. For example, the external device 16 can include any device that has internet capabilities 18, such as wife, etc., and a display 20. Information from the ear instrument assembly 10 can be communicated to the external device 16 via a network 22 through an internet connection and displayed in real time on the display 20 to assist the user in removing cerumen 14 from the ear canal. Non limiting examples of the external device 16 can include a computer, a cell phone, a tablet, a wall-mounted screen, any other internet based device, etc.

The external device 16 can include a processor 24 and a memory 26. The external device 16 is configured to execute the instructions from the memory 26, via the processor 24. For example, the external device 16 can be a host machine or distributed system, e.g., a computer such as a digital computer or microcomputer, and, as the memory 26, tangible, non-transitory computer-readable memory such as read-only memory (ROM) or flash memory. The external device 16 can also have random access memory (RAM), electrically erasable programmable read-only memory (EEPROM), a high-speed clock, analog-to-digital (A/D) and/or digital-to-analog (D/A) circuitry, and any required input/output circuitry and associated devices, as well as any required signal conditioning and/or signal buffering circuitry. Therefore, the external device 16 can include all software, hardware, memory 26, algorithms, connections, sensors, etc., necessary to communicate with the ear instrument assembly 10 and/or the network 22.

Referring to FIGS. 1-5, the ear instrument assembly 10 includes a base unit 28 and a tool 30 selectively coupled to the base unit 28. In certain embodiments, the tool 30 provides multiple functions. For example, the tool 30 can function as an otoscope 32 and a curette 34 (see FIGS. 6-9). It can be desirable to present an aesthetically pleasing configuration of the base unit 28 and the tool 30, which can comfort children. The aesthetically pleasing configuration can be a monkey and a banana, or any other child friendly configuration. The configuration of the base unit 28 and the tool 30 is discussed further below.

The base unit 28 is configured to be in communication with the external device 16. For example, the base unit 28 and the external device 16 can communicate through the internet connection. As best shown in FIG. 1, the base unit 28 includes a first housing 36 defining an opening 38. The base unit 28 can house various components (discussed further below) to provide communication with the tool 30 and to the external device 16.

Figure 4:
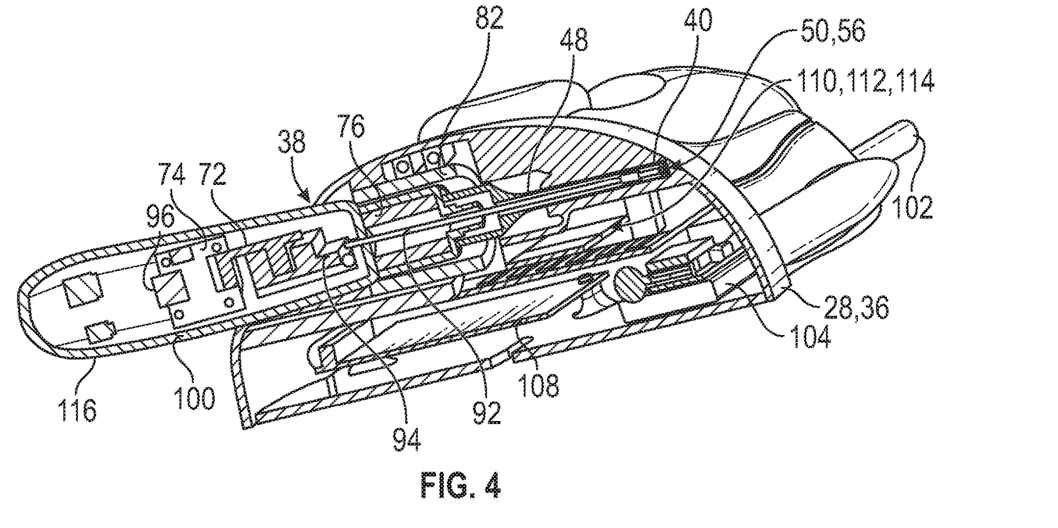
FIG. 4 is a schematic cross-sectional view of the base unit and the tool partially disposed inside the base unit in the storage position.
Figure 5:
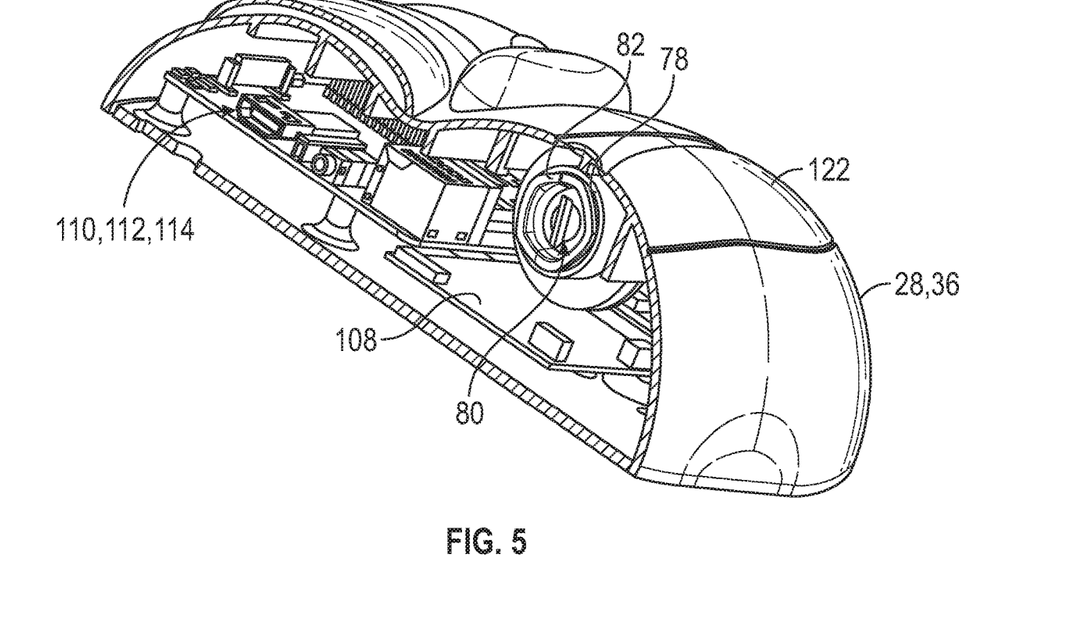
FIG. 5 is a schematic cross-sectional view of the base unit.
Figure 6:
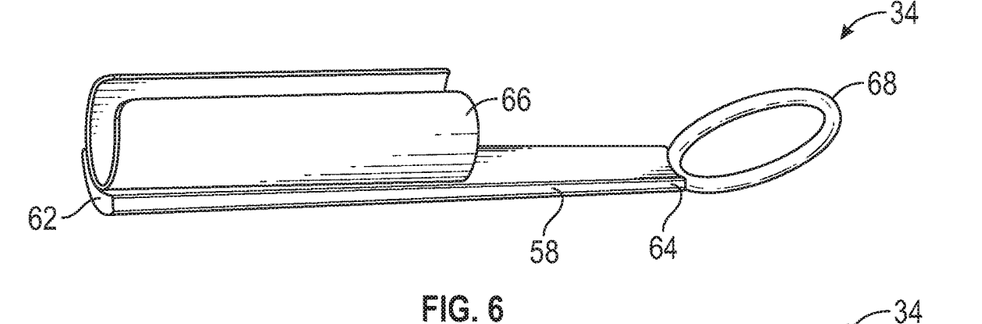
FIG. 6 is a schematic perspective view of a curette including an extractor member of a first configuration.
Figure 7:
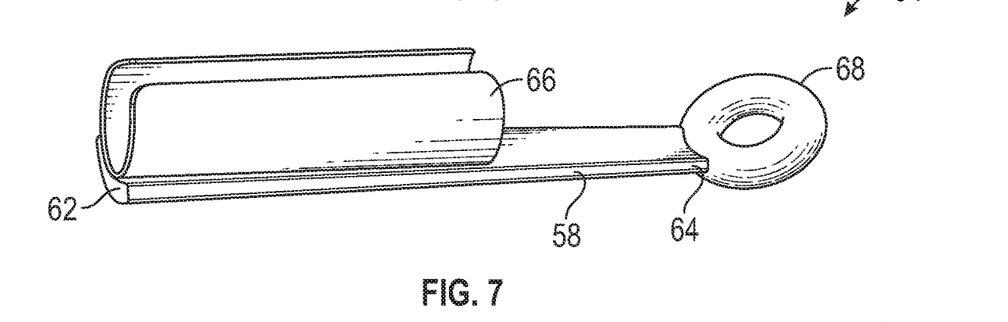
FIG. 7 is a schematic perspective view of a curette including an extractor member of a second configuration.
Figure 8:
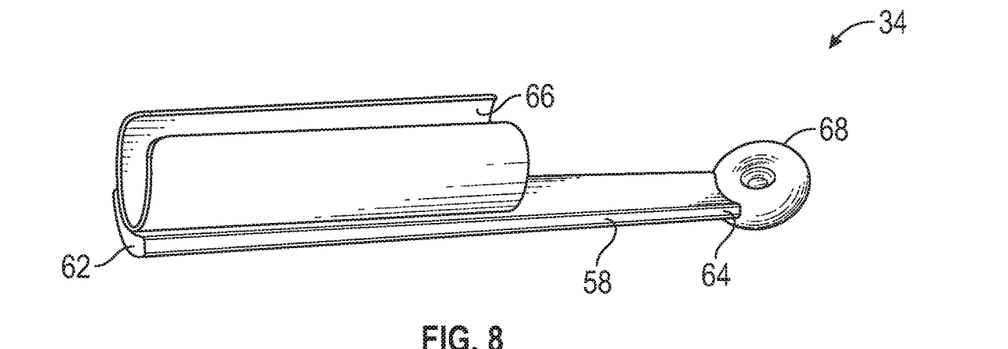
FIG. 8 is a schematic perspective view of a curette including an extractor member of a third configuration.
Figure 9:
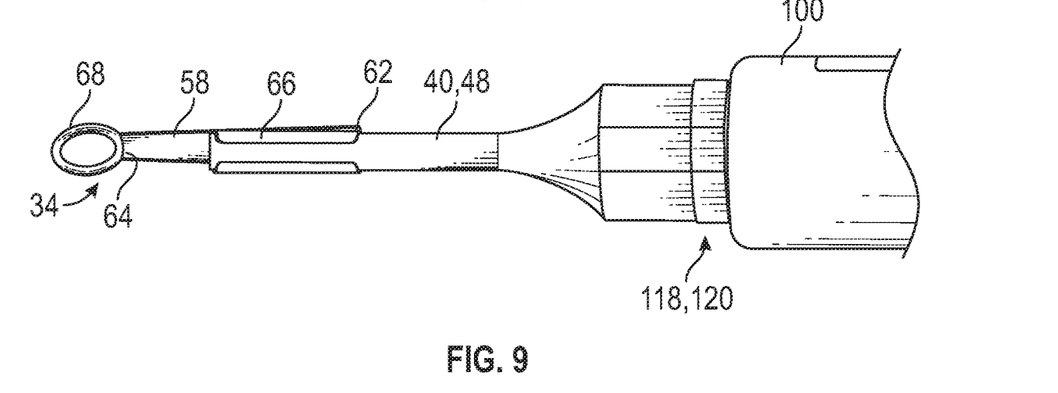
FIG. 9 is a schematic fragmentary view of the curette secured to a tip of the tool.

As mentioned above, the tool 30 can be selectively coupled to the base unit 28. The tool 30 can be utilized to view inside the channel 12 such as the ear canal, as well as remove cerumen 14. Generally, the tool 30 is movable between a storage position in which the tool 30 is partially disposed into the opening 38 and a use position in which the tool 30 is removed from the opening 38. Specifically, the tool 30 is movable between the storage position in which the tool 30 is partially disposed into the opening 38 such that the tool 30 is secured to the first housing 36 and the use position in which the tool 30 is removed from the opening 38 such that the tool 30 is spaced from the first housing 36. Therefore, the tool 30 cannot be operated when in the storage position and the tool 30 can be operated when in the use position. Furthermore, when the tool 30 is in the storage position, the tool 30 can be recharged, which is discussed further below. The storage position is shown in FIGS. 1 and 4. The use position is shown in FIG. 2.

Figure 2:
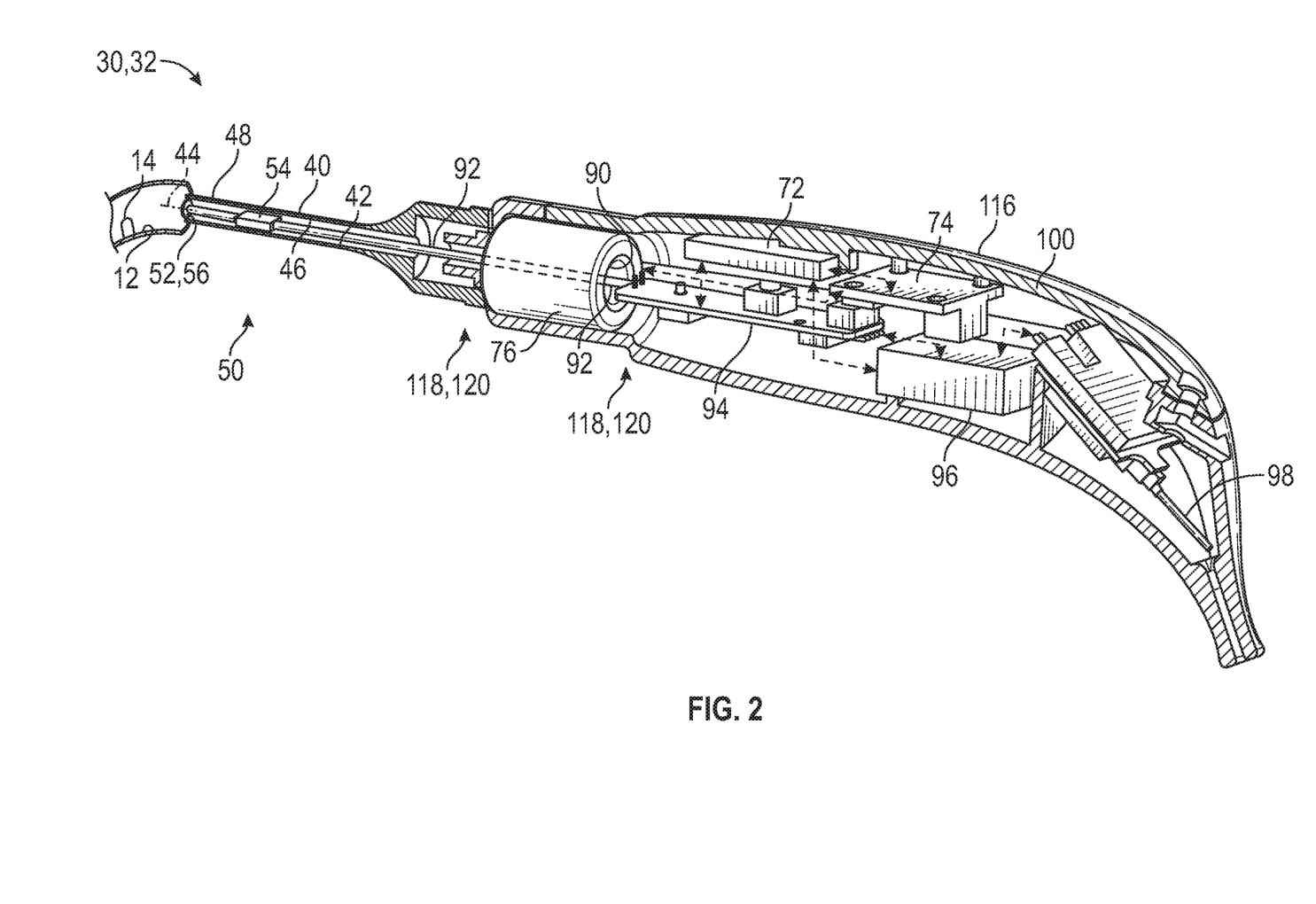
FIG. 2 is a schematic cross-sectional view of the tool of FIG. 1.

Referring to FIG. 2, the tool 30 includes a tip 40 that can be disposed inside the channel 12, such as the ear canal. Generally, the tip 40 is configured small enough to fit inside a child's ear. The tip 40 is contained inside the first housing 36 when the tool 30 is in the storage position. The first housing 36 can protect the tip 40 of the tool 30 when the tool 30 is not being utilized.

Referring to FIG. 2, the tip 40 of the tool 30 can define an aperture 42 along a central axis 44. As such, the tip 40 of the tool 30 can align on the central axis 44. In certain embodiments, the aperture 42 is coaxial with the central axis 44. Also referring to FIG. 10, the tip 40 can include an inner surface 46 defining an outer boundary of the aperture 42. The inner surface 46 can face the central axis 44. In addition, the tip 40 can include an outer surface 48 opposing the inner surface 46 and facing away from the inner surface 46.

Figure 10:
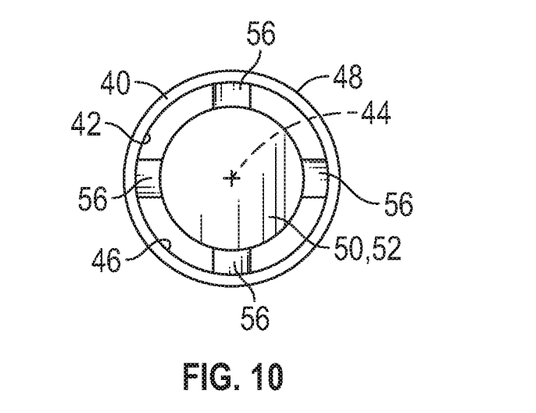
FIG. 10 is a schematic end view of the tip of the tool.
Figure 11:
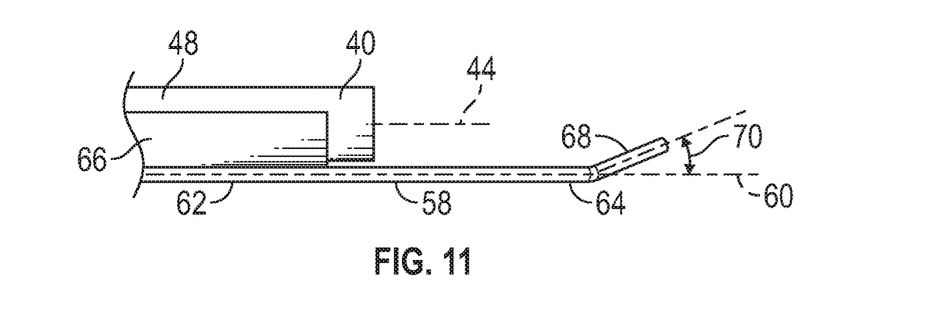
FIG. 11 is a schematic fragmentary side view of the tip of the tool with the curette extending from the tip.

Referring to FIGS. 2 and 10, the tool 30 includes a camera 50 at least partially disposed in the tip 40 of the tool 30. In certain embodiments, the camera 50 can be disposed in the aperture 42. Furthermore, in certain embodiments, the camera 50 can align coaxial with the central axis 44. The camera 50 is utilized to visualize or see inside the channel 12, such as the ear canal. For example, the camera 50 can view the ear canal, including the color of the ear canal, swelling in the ear canal and the tympanic membrane, to determine if the person has an ear infection, or some other condition. The camera 50 can include a lens 52, an image processor chip 54 and any other suitable camera components. The lens 52 and the image processor chip 54 can be disposed inside the tip 40 of the tool 30. In certain embodiments, a first side of the lens 52 can be substantially flush with a distal most end of the tip 40 of the tool 30. Any suitable camera 50 can be utilized, and a non-limiting example of the camera 50 can include an analog camera. As non-limiting examples, the analog camera can be a 3.9 millimeter lens analog camera, or a 3.94 millimeter lens analog camera. In various embodiments, the camera 50 can also be capable of other visualization techniques, such as performing an x-ray, ultrasound, infrared imaging, etc.

The tool 30 includes the curette 34 (see FIGS. 6-9) attachable to and detachable from the tip 40 of the tool 30. The curette 34 can be utilized to remove object(s), debris, material(s) and/or substance(s) from the channel 12. As one non-limiting example, the curette 34 can be utilized to remove cerumen 14 from the channel 12, such as the ear canal. The curette 34 can include a plurality of curettes 34 that are each attachable to and detachable from the tip 40 of the tool 30. Different configurations of curettes 34 can be utilized to remove various object(s), debris, material(s) and/or substance(s) from the channel 12 as discussed further below. The curette 34 is detachable to utilize the tool 30 without the curette 34, to interchange the curette 34 with different sizes or configurations, and/or to discard or clean the curette 34 after use.

Referring to FIG. 10, the tool 30 can further include a light 56 to illuminate the channel 12, such as the ear canal, which can improve the images from the camera 50 and/or can improve the ability to visualize object(s), debris, material(s) and/or substance(s) in the channel 12. Generally, the camera 50 and the light 56 can be disposed in the aperture 42. In certain embodiments, the light 56 can be disposed between the camera 50 and the inner surface 46 of the tip 40. More specifically, the light 56 can be disposed between the camera 50 and the inner surface 46 of the tip 40 such that the light 56 is spaced from the central axis 44. Specifically, the light 56 can be disposed between the lens 52 of the camera 50 and the inner surface 46 of the tip 40. In various embodiments, the camera 50 can align on the central axis 44 and the light 56 is spaced from the central axis 44.

Furthermore, in certain embodiments, the light 56 can include a plurality of lights 56, and the lights 56 can surround the camera 50. More specifically, the lights 56 can surround the lens 52 of the camera 50. In certain embodiments, the lights 56 are spaced from each other. The light(s) 56 can be any suitable configuration and any suitable type of light 56, such as light emitting diode (LED), incandescent light, fiber optic light, etc.

As best shown in FIGS. 6-9 and 11, the curette 34 can include an arm 58, and in certain embodiments, the arm 58 can extend along a longitudinal axis 60. The arm 58 can include a proximal end 62 and a distal end 64. The proximal and distal ends 62, 64 can be spaced from each other relative to the longitudinal axis 60. In certain embodiments, the longitudinal axis 60 can be substantially parallel to the arm 58. Furthermore, in various embodiments, the central axis 44 and the longitudinal axis 60 can be substantially parallel to each other.

Continuing with FIGS. 6-9 and 11, the curette 34 can include a fastener member 66 secured to the arm 58. The fastener member 66 can be attachable to and detachable from the tip 40 of the tool 30. More specifically, the fastener member 66 can be attachable to and detachable from the outer surface 48 of the tip 40 of the tool 30. In certain embodiments, the fastener member 66 can be secured to the proximal end 62 of the arm 58. As one non-limiting example, the fastener member 66 includes a c-shaped clip. The c-shaped clip can engage the outer surface 48 of the tip 40. The fastener member 66 can be any suitable configuration to secure the curette 34 to the tip 40 of the tool 30 and prevent the fastener member 66 from rotating about the central axis 44 during use of the tool 30. In other words, the fastener member 66 also prevents the curette 34 from undesirably spinning around the tip 40 of the tool 30. The curette 34 can also be affixed to a disposable sleeve or a cover that fits over the distal most end of the tip 40 of the tool 30 to act as a barrier to prevent object(s), debris, material(s) and/or substance(s) from entering the aperture 42 of the tip 40.

Continuing with FIGS. 6-9 and 11, the curette 34 can also include an extractor member 68 secured to the arm 58. More specifically, the extractor member 68 can be secured to the distal end 64 of the arm 58. The extractor member 68 and the fastener member 66 can be spaced from each other. Furthermore, the c-shaped clip and the extractor member 68 can be spaced from each other. The extractor member 68 is utilized to remove the object(s), debris, material(s) and/or substance (s) from the channel 12. As the tip 40 of the tool 30 moves, the camera 50 and the curette 34 correspondingly move. The extractor member 68 is disposed at a distance that allows partial visualization of the curette 34 via the camera 50 while also being able to visualize the ear canal or the cerumen 14. Therefore, the user can see into the channel 12 via the camera 50 during the cerumen 14 removal process with the extractor member 68 which minimizes touching unintended areas in the channel 12.

Different curettes 34 including different configurations of the extractor member 68 can be utilized to remove various object(s), debris, material(s) and/or substance(s) from the channel 12. Non-limiting examples of the extractor member 68 can include different sized rings, different sized scoops, different sized picks, different sized paddles, etc., and combinations thereof. Generally, the ring(s) has a hole with the ring surrounding the hole, and the scoop(s) does not have a hole. The scoop(s) can be curved similar to a spoon.

The extractor member 68 can extend from the arm 58 at different angles 70. Generally, the extractor member 68 can extend from the arm 58 at an angle 70 (see FIG. 11) that allows the camera 50 to still visualize the object(s), debris, material(s) and/or substance(s) in the channel 12 while utilizing the extractor member 68, which allows the user of the tool 30 to minimize touching of unintended surfaces inside the channel 12. As one non-limiting example, the extractor member 68 extends from the arm 58 at an angle 70 not equal to zero degrees relative to the longitudinal axis 60 and not equal to one-hundred eighty degrees relative to the longitudinal axis 60. As another non-limiting example, the extractor member 68 can include a ring (see FIGS. 6, 7 and 9) extending from the arm 58 at an angle 70 not equal to zero degrees relative to the longitudinal axis 60 and not equal to one-hundred eighty degrees relative to the longitudinal axis 60. As yet another non-limiting example, the extractor member 68 can include a scoop (see FIG. 8) extending from the arm 58 at an angle 70 not equal to zero degrees relative to the longitudinal axis 60 and not equal to one-hundred eighty degrees relative to the longitudinal axis 60. As yet other non-limiting examples, the extractor member 68 can extend from the arm 58 at an angle 70 greater than zero degrees and less than ninety degrees relative to the longitudinal axis 60, or at an angle 70 greater than two-hundred seventy degrees and less than three-hundred sixty degrees relative to the longitudinal axis 60. As yet another non-limiting example, the extractor member 68 can extend from the arm 58 at an angle 70 of zero degrees.

Referring to FIG. 2, the tool 30 can include a power source 72 that can power the camera 50 and the light(s) 56. Therefore, the camera 50 and the light(s) 56 can be electrically connected to the power source 72. As such, the power source 72 can supply power to operate the camera 50 and the light(s) 56. The power source 72 can include a battery. In certain embodiments, the battery is a rechargeable battery. It is to be appreciated that in certain embodiments, the battery can be a replaceable battery. Non-limiting examples of the battery can include a lithium ion battery, a lithium polymer battery, alkaline battery, zinc-carbon battery, etc.

Continuing with FIG. 2, the tool 30 can also include a charger 74 that are electrically connected to the power source 72, and can include coils 76 that are electrically connected to the power source 72. The coils 76 can also be electrically connected to the charger 74. Therefore, the coils 76 are electrically connected to the power source 72 through the charger 74. The coils 76 produce energy that is fed to the charger 74 and the charger 74 utilizes the energy from the coils 76 to recharge the power source 72 of the tool 30. When utilizing a rechargeable power source 72, the charger 74 can include an inductive charger 74. Therefore, the charger 74 of the tool 30 can include a lithium ion charger, a lithium polymer charger, etc.

The tool 30 can be recharged wirelessly from the base unit 28. The tool 30 is disposed in the storage position and the coils 76 of the tool 30 are energized from the base unit 28. Therefore, referring to FIG. 3, the base unit 28 can include a charger 78 defining an aperture 80. The coils 76 of the tool 30 align inside the aperture 80 of the charger 78 of the base unit 28 when the tool 30 is in the storage position. The coils 76 of the tool 30 are configured to receive energy from the charger 78 of the base unit 28 to charge the power source 72 of the tool 30. More specifically, the charger 78 of the base unit 28 can include coils 82 defining the aperture 80, and the coils 76 of the tool 30 can be disposed inside the aperture 80 of the coils 82 of the base unit 28 when the tool 30 is in the storage position. The coils 82 of the base unit 28 can be energized which energizes the coils 76 of the tool 30, and energy from the coils 76 of the tool 30 is fed to the charger 74 of the tool 30 which charges the power source 72 of the tool 30.

The base unit 28 can power the charger 78 through a power cord 84 (see FIG. 3) receiving current from an outlet or a rechargeable power source 72. Power or current through the power cord 84 is directed to the charger 78 of the base unit 28 which energizes the coils 82 of the base unit 28 which causes the coils 76 of the tool 30 to receive energy from the coils 82 of the base unit 28 to charge the power source 72 of the tool 30. The charger 78 of the base unit 28 can include an inductive charger. Therefore, the charger 78 of the base unit 28 can include a lithium ion charger, a lithium polymer charger, etc. The power cord 84 can be in electrical communication with a battery charger 86 and a battery charge indicator 88.

Referring to FIG. 2, in certain embodiments, the coils 76 of the tool 30 can define a hole 90. In various embodiments, the hole 90 of the coils 76 can be coaxial with the central axis 44. The tool 30 can include a wire harness 92 disposed through the hole 90 to electrically connect the camera 50 to the power source 72. In certain embodiments, the wire harness 92 of the tool 30 can be disposed through the hole 90 to electrically connect the camera 50 and the light 56 to the power source 72. The wire harness can include one or more wires to electrically connect various components, such as the camera 50, the lens 52, the image processor chip, the light 56, etc., together.

Continuing with FIG. 2, the tool 30 can include a charge-couple-device (CCD) camera module 94 in communication with the camera 50. More specifically, the CCD camera module 94 can be in communication with the lens 52 and the image processor chip 54. The CCD camera module 94 gathers and/or processes data from the camera 50, and more specifically from the image processor chip 54. Therefore, the wire harness 92 electrically connects the camera 50 and the CCD camera module 94. The power source 72 can supply power to operate the CCD camera module 94. Therefore, the CCD camera module 94 is electrically connected to the power source 72. In certain embodiments, the camera 50 can include the CCD camera module 94.

Continuing with FIG. 2, the tool 30 can include a transmitter 96 in communication with the CCD camera module 94. The CCD camera module 94 and the transmitter 96 are electrically connected to the power source 72. The transmitter 96 of the tool 30 can also be electrically connected to the power source 72. Therefore, the power source 72 can supply power to operate the transmitter 96. As such, the power source 72 can supply power to operate the camera 50, the light(s) 56, and the transmitter 96. The transmitter 96 can be an analog transmitter 96 or any other suitable transmitter 96.

Continuing with FIG. 2, the tool 30 can include an antenna 98 configured to transmit data gathered from the camera 50. Specifically, the antenna 98 can be in communication with the transmitter 96 to transmit data gathered from the camera 50. The antenna 98 of the tool 30 can be referred to as a transmitter antenna.

The tool 30 can include a second housing 100 that can house various components. For example, the tool 30 can house the power source 72, the charger 74, the coils 76, the wire harness 92, the transmitter 96 and the antenna 98. The tool 30 is compact and is not hardwired to the base unit 28. Therefore, if a plurality of ear instrument assemblies 10 are being utilized, any of these tools 30 can be compatible with any of the base units 28. In other words, the tools 30 and the base units 28 are interchangeable with other tools 30 and other base units 28. Furthermore, in various embodiments, the curette 34 can move independently of the camera 50 and/or the lens 52; or the tip 40 of the tool 30 can move independently of the second housing 100.

Figure 3:
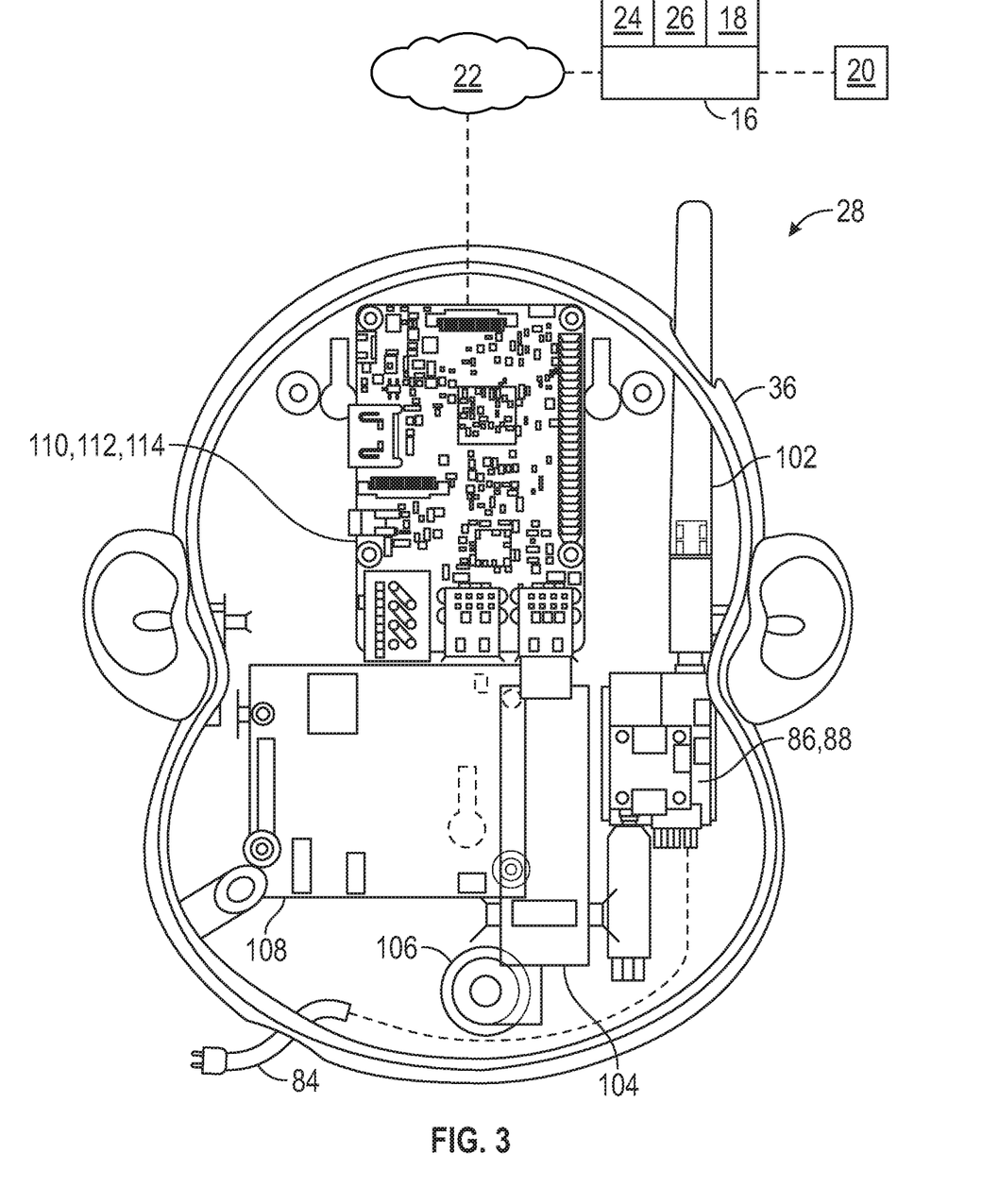
FIG. 3 is a schematic cross-sectional view of the base unit of FIG. 1.

Referring to FIG. 3, the base unit 28 can include an antenna 102 configured to receive the data from the antenna 98 of the tool 30 regarding the data gathered by the camera 50. Therefore, the antenna 102 of the base unit 28 can be referred to as a receiver antenna.

Continuing with FIG. 3, the base unit 28 can also include a receiver 104 in communication with the antenna 98 of the base unit 28, and can include a voltage divider 106 in communication with the receiver 104. Furthermore, the base unit 28 can include a screen decoding board 108 in communication with the voltage divider 106. The screen decoding board 108 converts the analog signal from the antenna 98 of the tool 30 to a digital signal. Additionally, the base unit 28 can include a controller 110 having a processor 112 in communication with the screen decoding board 108. The controller 110 can also include a memory 114. The controller 110 processes the digital signal from the screen decoding board 108. The controller 110 also has internet capabilities 18 and can communicate with the network 22 such that the data/information, for example images, gathered via the tool 30 can be viewed on an external device 16 through a website or streamed live on the website. Therefore, the controller 110 can be configured to stream the data from the camera 50 to the external device 16 that displays 20 the data from the camera 50. In certain embodiments, the controller 110 can be a computer, and the computer can stream the data from the camera 50 to the external device 16. Therefore, the controller 110 can livestream the data from the camera 50 to any wifi-enabled external device that displays the data from the camera 50. The online interface streaming the camera data is encrypted to secure patient information and allow images of the patient's ear to be captured and added to the patient's record. The display 20 can be configured to display 20 the data from the camera 50. Each tool 30 can include a unique bar code, for example a matrix barcode such as a quick response (QR) code, which is communicated through the base unit 28 to the external device 16 to ensure that the desired information/data is being displayed on the display 20.

The controller 110 is configured to execute the instructions from the memory 114, via the processor 112. For example, the controller 110 can be a host machine or distributed system, e.g., a computer such as a digital computer or microcomputer, and, as the memory 114, tangible, non-transitory computer-readable memory such as read-only memory (ROM) or flash memory. The controller 110 can also have random access memory (RAM), electrically erasable programmable read-only memory (EEPROM), a high-speed clock, analog-to-digital (A/D) and/or digital-to-analog (D/A) circuitry, and any required input/output circuitry and associated devices, as well as any required signal conditioning and/or signal buffering circuitry. Therefore, the controller 110 can include all software, hardware, memory 114, algorithms, connections, sensors, etc., necessary to communicate with the tool 30, the network 22 and/or the external device 16.

The first housing 36 of the base unit 28 can house various components. For example, the first housing 36 can house the receiver 104, the voltage divider 106, the screen decoding board 108, the controller 110, such as the computer, the charger 78 and the coils 82. Furthermore, the first housing 36 can at least partially house the antenna 102. The first housing 36 defines the opening 38 that receives the tool 30. The tool 30 is inserted into the opening 38 without the curette 34 being attached to the tip 40. In other words, the curette 34 is removed before placing the tool 30 in the storage position.

The tool 30 is grasped differently than traditional otoscopes 32. Traditional otoscopes 32 are grasped similar to a hammer, with all of the fingers of the user wrapping around a handle of the otoscope 32. The tool 30 described herein is grasped similar to a pencil or a pen, with the thumb and the index finger of the user pinching the tool 30. Therefore, the tool 30 can be grasped and used in a manner as if writing with a pencil or a pen. By grasping/using the tool 30 in this pencil/pen manner, fine movements of the tool 30 can be achieved.

Referring to FIG. 2, the tool 30 can be grasped in a certain manner to examine the channel 12 and/or use the curette 34. Therefore, the second housing 100 can include an outer surface 116 spaced from the central axis 44 and facing away from the central axis 44. The outer surface 116 of the second housing 100 can be utilized to grasp the tool 30. At least one of the tip 40 and the second housing 100 can include a grip 118 disposed along the outer surface 116 and configured to move the camera 50. As such, the tip 40 can include the grip 118, or the second housing 100 can include the grip 118, or the tip 40 and the second housing 100 can each include the grip 118. More specifically, the outer surface 48 of the tip 40 can include the grip 118, or the outer surface 116 of the second housing 100 can include the grip 118, or the outer surface 48 of the tip 40 and the outer surface 116 of the second housing 100 can each include the grip 118. In certain embodiments, the grip 118 can be partially disposed coaxial with the central axis 44. The location of the grip 118 is positioned to allow the tool 30 to be grasped and used in the pencil/pen manner discussed above.

Optionally, at least one of the tip 40 and the second housing 100 can include a step 120 spaced from the central axis 44. As such, the tip 40 can include the step 120, or the second housing 100 can include the step 120, or the tip 40 and the second housing 100 can each include the step 120. Generally, the step 120 can be disposed along the outer surface 116 of the tool 30. In certain embodiments, the grip 118 can be disposed along at least a portion of the step 120. Furthermore, more than one step 120 can be utilized to provide different grip 118 locations. As such, more than one grip 118 can be provided on the tool 30 which provides different accommodations for the user to grasp the tool 30.

It can be desirable to present an aesthetically pleasing configuration to the base unit 28 and the tool 30, which can comfort children. For example, as shown in FIG. 1, the first housing 36 of the base unit 28 can include a face 122 configured as a monkey face, and the second housing 100 of the tool 30 can be configured as a banana. More specifically, the outer surface 116 of the second housing 100 can be configured as the banana. It is to be appreciated that the face 122 of the base unit 28 and the second housing 100 of the tool 30 can be other configurations, including other configurations pleasing to children.

While the best modes and other embodiments for carrying out the disclosure have been described in detail, those familiar with the art to which this disclosure relates will recognize various alternative designs and embodiments for practicing the disclosure within the scope of the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

The invention claimed is:

1. An ear instrument assembly comprising:
    a base unit including a first housing defining an opening;
    a tool movable between a storage position in which the tool is partially disposed into the opening such that the tool is secured to the first housing and a use position in which the tool is removed from the opening such that the tool is spaced from the first housing;
    wherein:
        the tool includes a tip contained inside the first housing when the tool is in the storage position;
        the tool includes a camera at least partially disposed in the tip of the tool, and the tool includes a curette attachable to and detachable from the tip of the tool;
        the tip of the tool defines an aperture along a central axis;
        the camera is aligned coaxial with the central axis;
        the tip includes an inner surface defining an outer boundary of the aperture;
        the tip includes an outer surface opposing the inner surface and facing away from the inner surface;
        the tool further includes a light disposed between the camera and the inner surface of the tip such that the light is spaced from the central axis;
        the camera and the light are disposed in the aperture;
        the curette includes an arm extending along a longitudinal axis and includes a fastener member secured to the arm;
        the fastener member is attachable to and detachable from the outer surface of the tip of the tool;

the fastener member includes a c-shaped clip;
the curette includes an extractor member secured to the arm;
the c-shaped clip and the extractor member are spaced from each other;
the extractor member extends from the arm at an angle not equal to zero degrees relative to the longitudinal axis and not equal to one-hundred eighty degrees relative to the longitudinal axis;
the tool includes a power source and coils that are electrically connected to the power source;
the coils define a hole coaxial with the central axis; and
the tool includes a wire harness disposed through the hole to electrically connect the camera and the light to the power source.

2. The assembly as set forth in claim 1 wherein the inner surface faces the central axis.

3. The assembly as set forth in claim 1 wherein:
the arm includes a proximal end and a distal end, with the fastener member secured to the proximal end;
the extractor member is secured to the distal end of the arm; and
the extractor member and the fastener member are spaced from each other.

4. The assembly as set forth in claim 3 wherein the extractor member includes a ring extending from the arm at an angle not equal to zero degrees relative to the longitudinal axis and not equal to one-hundred eighty degrees relative to the longitudinal axis.

5. The assembly as set forth in claim 3 wherein the extractor member includes a scoop extending from the arm at an angle not equal to zero degrees relative to the longitudinal axis and not equal to one-hundred eighty degrees relative to the longitudinal axis.

6. The assembly as set forth in claim 1 wherein the tip of the tool aligns on the central axis.

7. The assembly as set forth in claim 6 wherein the tool includes:
a charge-couple-device (CCD) camera module in communication with the camera, and the wire harness electrically connects the camera and the CCD camera module;
a transmitter in communication with the CCD camera module, with the CCD camera module and the transmitter electrically connected to the power source; and
an antenna in communication with the transmitter to transmit data gathered from the camera.

8. The assembly as set forth in claim 1 wherein the tool includes an antenna configured to transmit data gathered from the camera, and wherein the base unit includes an antenna configured to receive the data from the antenna of the tool regarding the data gathered by the camera.

9. The assembly as set forth in claim 8 wherein the base unit includes:
a receiver in communication with the antenna of the base unit;
a voltage divider in communication with the receiver;
a screen decoding board in communication with the voltage divider; and
a computer in communication with the screen decoding board, and wherein the computer is configured to stream the data from the camera to an external device separate from the base unit.

10. The assembly as set forth in claim 1 wherein:
the base unit includes a charger defining an aperture;
the power source and the coils are configured to receive energy from the charger of the base unit to charge the power source of the tool; and
the coils of the tool align inside the aperture of the charger of the base unit when the tool is in the storage position.

11. The assembly as set forth in claim 1 wherein the tip of the tool aligns on the central axis, and the tool includes a second housing having an outer surface spaced from the central axis and facing away from the central axis, and wherein at least one of the tip and the second housing includes a grip disposed along the outer surface and configured to move the camera.

12. The assembly as set forth in claim 11 wherein at least one of the tip and the second housing includes a step spaced from the central axis, with the grip disposed along at least a portion of the step.

13. The assembly as set forth in claim 11 wherein the grip is partially disposed coaxial with the central axis.

14. The assembly as set forth in claim 1 wherein the first housing of the base unit includes a face configured as a monkey face, and wherein the tool includes a second housing that is configured as a banana.

15. The assembly as set forth in claim 1 wherein the tool includes:
a charge-couple-device (CCD) camera module in communication with the camera and the wire harness electrically connects the camera and the CCD camera module;
a transmitter in communication with the CCD camera module, with the CCD camera module and the transmitter are electrically connected to the power source; and
an antenna in communication with the transmitter to transmit data gathered from the camera.

16. An ear instrument assembly in communication with an external device, the ear instrument assembly comprising:
a base unit configured to be in communication with the external device, and the base unit includes a first housing defining an opening;
a tool movable between a storage position in which the tool is partially disposed into the opening such that the tool is secured to the first housing and a use position in which the tool is removed from the opening such that the tool is spaced from the first housing;
wherein:
the tool includes a tip contained inside the first housing when the tool is in the storage position;
the tool includes a camera at least partially disposed in the tip of the tool, and the tool includes a curette attachable to and detachable from the tip of the tool;
the tip of the tool defines an aperture coaxial with a central axis;
the camera is aligned coaxial with the central axis;
the tip includes an inner surface defining an outer boundary of the aperture, with the inner surface facing the central axis;
the tip includes an outer surface opposing the inner surface and facing away from the inner surface;
the tool further includes a light disposed between the camera and the inner surface of the tip;
the camera and the light are disposed in the aperture;
the curette includes an arm extending along a longitudinal axis and includes a fastener member secured to the arm;
the fastener member is attachable to and detachable from the outer surface of the tip of the tool;
the fastener member includes a c-shaped clip;

the curette includes an extractor member secured to the arm;

the c-shaped clip and the extractor member are spaced from each other;

the extractor member extends from the arm at an angle not equal to zero degrees relative to the longitudinal axis and not equal to one-hundred eighty degrees relative to the longitudinal axis;

the tool includes a power source and coils that are electrically connected to the power source;

the coils define a hole coaxial with the central axis; and the tool includes a wire harness disposed through the hole to electrically connect the camera and the light to the power source;

the tool includes a charge-couple-device (CCD) camera module in communication with the camera, and the wire harness electrically connects the camera and the CCD camera module;

the tool includes a transmitter in communication with the CCD camera module, with the CCD camera module and the transmitter are electrically connected to the power source;

the tool includes an antenna in communication with the transmitter to transmit data gathered from the camera;

the base unit includes an antenna configured to receive the data from the antenna of the tool regarding the data gathered by the camera;

the base unit includes a receiver in communication with the antenna of the base unit;

the base unit includes a voltage divider in communication with the receiver;

the base unit includes a screen decoding board in communication with the voltage divider;

the base unit includes a controller having a processor in communication with the screen decoding board, and the controller is configured to stream the data from the camera to the external device that displays the data from the camera;

the first housing of the base unit includes a face configured as a monkey face; and the tool includes a second housing that is configured as a banana.

\* \* \* \* \*